United States Patent [19]

Süling et al.

[11] 4,300,886

[45] Nov. 17, 1981

[54] SHAPED DENTAL ARTICLES

[75] Inventors: Carlhans Süling, Odenthal; Gerhard Ballé; Bernd Leusner, both of Leverkusen; Hans-Hermann Schulz, Leichlingen; Michael Walkowiak, Cologne, all of Fed. Rep. of Germany

[73] Assignee: Bayer Aktiengesellschaft, Leverkusen, Fed. Rep. of Germany

[21] Appl. No.: 158,031

[22] Filed: Jun. 9, 1980

Related U.S. Application Data

[63] Continuation of Ser. No. 959,548, Nov. 13, 1978, abandoned.

[30] Foreign Application Priority Data

Nov. 25, 1977 [DE] Fed. Rep. of Germany ....... 2752611

[51] Int. Cl.³ .................... C08L 75/00; A61C 13/00; A61C 13/22
[52] U.S. Cl. ............................ 433/202; 260/998.11; 433/171; 525/440; 525/455; 525/920
[58] Field of Search .................. 260/998.11; 525/440, 525/455

[56] References Cited

U.S. PATENT DOCUMENTS

| | | | |
|---|---|---|---|
| 4,073,828 | 2/1978 | Ferrarini et al. | 260/859 R |
| 4,089,763 | 5/1978 | Dart | 260/859 R |
| 4,110,184 | 8/1978 | Dart | 260/859 R |
| 4,134,930 | 1/1979 | Kubota | 260/998.11 |
| 4,134,935 | 1/1979 | Quiring | 260/998.11 |
| 4,223,114 | 9/1980 | Suling | 525/455 |
| 4,233,424 | 11/1980 | Suling | 525/455 |
| 4,233,436 | 11/1980 | Robinson | 525/440 |
| 4,243,578 | 1/1981 | O'Sullivan | 525/455 |

FOREIGN PATENT DOCUMENTS

| | | | |
|---|---|---|---|
| 1373182 | 11/1974 | United Kingdom | 260/859 R |
| 1409282 | 10/1975 | United Kingdom | 260/859 R |

*Primary Examiner*—Paul Lieberman
*Attorney, Agent, or Firm*—Sprung, Felfe, Horn, Lynch & Kramer

[57] ABSTRACT

The invention relates to bead polymers, useful in the provision of dental articles and made by bead polymerizing a diamine-lengthened polyurethane and a methacrylate. Also included in the invention are the dental articles made using said bead polymers.

4 Claims, No Drawings

SHAPED DENTAL ARTICLES

This is a continuation of Application Ser. No. 959,548, filed Nov. 13, 1978 now abandoned.

The invention relates to polymethacrylate dental articles (for example dentures, crowns or bridges) with improved mechanical properties to materials for making such articles and to methods for making such articles using such materials.

It is conventional to make dentures of plastic by means of the so-called powder-liquid process (German Pat. No. 737,058).

In an embodiment of this procedure, a bead polymer based on a polymethacrylate is processed, together with a methacrylate, for example methyl methacrylate, to form a paste by stirring 2 to 3 parts of the powder with 1 part of liquid. A peroxide is added to the monomer before preparing the paste, so that after the paste has been put into a hollow mould it can be hardened by heating, the monomer being polymerised.

Because such a preparation process for dentures, crowns and bridges is easy to carry out, the powder-liquid process has become the standard technique for preparing plastic dentures. It is known to improve the processability of dental beads in the powder-liquid process by using polymethyl methacrylate powder, preferably in the form of polymethyl methacrylate beads of a definite particle size, and it is also known to improve the processing procedure of dental beads by using as the powder beads consisting of copolymers of methyl methacrylate with a predominant proportion of copolymerised methacrylic acid methyl ester (instead of polymethyl methacrylate beads). These variations make it possible to improve the rapidity of the process and to make possible a broad spectrum of process conditions.

A disadvantage of the dentures, crowns and bridges based on polymethyl methacrylate and prepared by the powder-liquid process is that the mechanical values of the raw material are not satisfactory for many structures. In particular, in many cases the toughness properties of the plastic under load are not sufficient for dentures, crowns and bridges. Improving the impact strength of the plastic would have the effect of lowering the tendency of the dentures to break and also, therefore, of making it possible to carry out of the cleaning operation more reliably.

The present invention is based on the surprising discovery that shaped dental articles prepared by the powder-liquid process, such as dentures, bridges and crowns based on polymethacrylates, have improved mechanical properties and retain other desirable properties if polymethyl methacrylates which have been elasticized by means of diamine-lengthened polyurethanes are used as the powder or as a component thereof.

Such substances are also a suitable component of materials for repairing dentures, bridges and browns.

The invention therefore provides shaped polymethacrylate dental articles in which the polymethacrylate is an elasticized polymethacrylate elasticated by means of a diamine-lengthened polyurethane.

The invention also provides dental articles of this type, in which the elasticated polymethacrylate has been obtained by bead polymerisation of (A) 88 to 99.5% by weight of a polymer consisting of polymerised units of at least one methacrylic acid ester with 1 to 10 C atoms in the aliphatic, saturated alcohol component, it being possible for the methacrylic ester polymer to contain up to 30% by weight of copolymerised units of at least one monomer from the group comprising acrylic acid esters with 1 to 10 C atoms in the aliphatic, saturated alcohol component, hydroxyalkyl esters of acrylic acid or methacrylic acid with 2 to 4 C. atoms in the alkyl group, styrene, vinyl acetate (meth) acrylamide, (meth)acrylic acid and/or itaconic acid, and (B) 0.5 to 12% by weight of a diamine-lengthened polyurethane which has been obtained from (1) at least one dihydroxy compound,
(2) diisocyanates from the group comprising (a) aliphatic diisocyanates with a branched carbon skeleton of 7 to 36 C atoms, (b) cycloaliphatic diisocyanates and (c) aliphatic or cycloaliphatic diisocyanates modified with vinyl monomers by free radical grafting copolymerisation, and
(3) aliphatic or cycloaliphatic diamines and chain stoppers containing monofunctional, optionally unsaturated groups.

The invention also provides a process for preparing dental beads which comprises bead polymerising a diamine-lengthened polyurethane and a methacrylate whereby elasticized polymethacrylate dental beads are obtained.

The invention also provides material for making dental articles comprising such dental beads, optically in admixture with non-elasticized beads, as well as a method for preparing dental articles which comprises subjecting such dental beads to moulding and hardening by the powder-liquid process. The dental articles may, if desired, be made by subjecting to moulding and hardening by the powder-liquid process acrylate chips comprising elasticized polymethacrylate elasticized by means of diamine-lengthened polymethane.

It is known to elasticize polymethyl methacrylates by polymerising the methyl methacrylate by the bulk polymerisation process, whilst simultaneously shaping. However, it was not to be expected that dentures with improved properties can be obtained if the powder-liquid process is used and a polymethyl methacrylate which contains a diamine-lengthened polyurethane as an elastifying component is employed as the powder.

As is generally known, dental plastics which are obtained by the powder-liquid process are characterised by a particular structure. A multi-phase system, which can be detected by special methods, exists in the hardened plastic: only some of the original "liquid" has penetrated into the powder particles during the initial swelling procedure. A large, if not predominant, proportion of the liquid polymerises as a phase in itself and fills the intermediate spaces between the swollen original powder particles. The structure of shaped articles which consist of polymethacrylates or modified polymethyl methacrylate and which have been obtained by the powder-liquid process is thus substantially different to that of shaped articles which consist of polymethyl methacrylates and which have been obtained by customary shaping processes.

It is indeed also known, from German Pat. No. 940,493, to improve the mechanical values of shaped articles consisting of methyl methacrylates, by using mixtures of different polymers or copolymers as the powder components. For example, copolymers consisting of 80% of methyl methacrylate and 20% of butadiene are used for improving the flexural endurance. However, because of the butadiene content, copolymers of this type have a poor fastness to light.

Furthermore, it is known, from German Pat. No. 940,493, to use post-chlorinated polyvinyl chloride as an additive in order to improve the flexural impact strength and the flexural endurance of shaped articles which are based on methyl methacrylate polymers and which have been obtained by the powder-liquid process. However, using post-chlorinated polyvinyl chlorides as an additive has the effect of lowering the resistance towards discoloration. Moreover, the stability of post-chlorinated polyvinyl chlorides is not sufficient when relatively active peroxides or relatively high polymerisation temperatures are used.

Shaped articles for dental purposes, such as dentures, bridges or crowns, based on organic plastics can be prepared by various procedures.

Thus, for example, it is possible to convert the plastic into the desired shaped articles via an injection or extrusion process.

The dentures, bridges, crowns or teeth according to the invention are obtained by this process by shaping polymethacrylates which are elasticized by diamine-lengthened polyurethanes and are optionally mixed with customary "injectable" polymethyl methacrylates, by means of an injection device or by means of an extrusion device.

However, a particularly versatile process for the preparation of dentures, crowns or bridges is the powder-liquid process. The shaped articles according to the invention are obtained by this process by using a polymethacrylate elasticized by diamine-lengthened polyurethane as the powder. These powders can be obtained by converting polymethacrylates elasticized by diamine-lengthened polyurethanes into so-called "acrylate chips" via a comminuting process. However, particularly good results are obtained when those elasticized polymethacrylate powders which have been prepared by the procedure of a bead polymerisation and which consist of (A) 88 to 99.5% by weight of a polymer consisting of polymerised units of at least one methacrylic acid ester with 1 to 10 C atoms in the aliphatic, saturated alcohol component, it being possible for the methacrylic ester polymer to contain up to 30% by weight of copolymerised units of at least one monomer from the group comprising acrylic acid esters with 1 to 10 C atoms in the aliphatic, saturated alcohol component, hydroxyalkyl esters of acrylic acid or methacrylic acid with 2 to 4 C atoms in the alkyl group, styrene, vinyl acetate, (meth)acrylamide, (meth)acrylic acid and/or itaconic acid, and (B) 0.5 to 12% by weight of a diamine-lengthened polyurethane which has been obtained from (1) at least one dihydroxy compound, (2) diisocyanates from the group comprising (a) aliphatic (particularly alkyl) diisocyanates with a branched carbon skeleton of 7 to 36 C atoms, (b) cycloaliphatic (particularly $C_4$–$C_6$-cycloalkyl) diisocyanates and (c) said aliphatic or cycloaliphatic diisocyanates modified with vinyl monomers by free radical grafting copolymerisation, and (3) said aliphatic (particularly alkyl) or cycloaliphatic (particularly $C_4$–$C_6$-cycloalkyl)diamines and chain stoppers containing monofunctional, optionally unsaturated groups, are used.

In addition to the better processability compared with the acrylate chips, the use according to the invention of the elasticized polymer beads additionally has the advantage that the elasticizing component is better protected against degradation by components in the medium of the mouth and is generally protected against the action of components in the medium of the mouth. In the dental beads, the diamine-lengthened polyurethane present as a separate phase is enveloped by the base substance of the dental beads, that is to say, the polymethacrylate, and is thus protected from such action. In addition, the dental beads are themselves also in turn embedded in a matrix of polymethacrylate and are thus protected.

A particular embodiment of the procedure according to the invention, for the preparation of dentures, crowns or bridges by the powder-/liquid process consists in setting up the desired processability and the required processing spectrum by using elasticized dental beads of a definite particle size, or by adjusting the initial swelling behaviour of the polymer beads by using comonomers in the bead polymerisation. However, it is very particularly advantageous to set up the characteristic quantities of processability and processing spectrum, which are particularly important for handling from the point of view of dentistry, by adding non-elasticized beads. It was surprising that the good elasticizing activity of the dental beads is not lowered when the latter are used as a mixture with customary dental beads. The mixing ratios most favourable technologically must nevertheless be determined from case to case and depend on the construction and on the function of the denture or bridge.

Polymethacrylates in the sense of the present invention are understood as polymerisation products of methacrylic acid esters. In most cases, methacrylic acid methyl ester is the main component, but useful results are also obtained with polyfunctional esters of methacrylic acid, and for specific purposes, good results are given by, for example, bis-GMA or its modification products and also the comonomers mentioned in U.S. Pat. No. 3,730,947.

Diamine-lengthened polyurethanes according to the present invention are polyurethane-polyurea elastomers which contain, as the hard segment, urea groups in a polyurethane chain. The urea groups are introduced into the polyurethane chains by using diamines as chain lengtheners.

The polyurethane-urea elastomers used are prepared, in accordance with methods customary in polyurethane chemistry, by polyaddition by the so-called one shot process, in which all the components are brought together and are reacted in one step to give the finished polyurethane-urea, or by the two-stage or prepolymer process. In the case of the latter process, which is preferred here, a prepolymer with terminal isocyanate groups is first produced from the diol component or components and a stoichiometric excess of the diisocyanate, and is lengthened in a second stage by reaction with the diamine.

Representatives of the starting components to be used for the preparation of the polyurethanes to be used according to the invention are described, for example, in High Polymers, volume XVI, "Polyurethanes, Chemistry and Technology", complied by Saunders-Frisch, Interscience Publishers, New York, London, volume I, 1962, pages 32–42 and pages 44–54 and volume II, 1964, pages 5–6 and 198–199, and in the Kunststoff-Handbuch (Plastics Handbook), volume VII, Vieweg-Höchtlen, Carl-Hanser-Verlag, Munich, 1966, for example on pages 45 to 71.

The choice of suitable diisocyanate is restricted by the requirement of high fastness to light, which is achieved by using aliphatic or alicyclic diisocyanates, and furthermore, by the fact that the acrylic acid esters and methacrylic acid esters used as solvents for the polyurethane-urea elastomer, in particular methyl methacrylate, are thermodynamically poor solvents for the elastomer. This manifest itself, on the other hand, in the sharp increase in viscosity with increasing content of urea groups in the polymer chain, and on the other hand, using aliphatic diisocyanates with a linear chain structure leads to turbid solutions. This is attributed to the fact that, because of the lack of steric hindrance, the polyurea segments formed associate so greatly that they crystallise out of the solution to a certain extent. The polymers resulting from the solutions are thereby also obtained in a turbid form. This is the case, for example, with the aliphatic diisocyanate hexamethylene-diisocyanate, which is most frequently used industrially. Possible diisocyanates for the preparation of the polyurethane-urea elastomer solutions according to the invention are therefore those aliphatic diisocyanates which have a relatively complex, non-linear structure and thus assist in finding a compromise between the association of the urea segments with one another, which is in itself desired, and the optical nature of the product. These are:

(A) aliphatic (particularly alkyl)diisocyanates having a branched carbon skeleton with 7 to 36 C atoms, for example 2,2,4- or 2,4,4-trimethylhexane-1,6-diisocyanate or industrial mixtures thereof, diisocyanates derived from esters of lysine or diisocyanates based on dimerised fatty acids, which are prepared in a known manner by conversion of dicarboxylic acids of this type with up to 36 C atoms into the corresponding diamines and subsequent phosgenation.

(B) cycloaliphatic (particularly $C_4$–$C_6$-cycloalkyl) diisocyanates for example cyclobutane-1,3-diisocyanate, cyclohexane-1,3- and 1,4-diisocyanate, 2,4- or 2,6-diisocyanato-1-methylcyclohexane or 4,4'-diisocyanatodicyclohexylmethane, either in the form of the pure geometric isomers or as industrial mixtures thereof, and furthermore, 1-isocyanato-3,3,5-trimethyl-5-isocyanatromethylcyclohexane (isophorone diisocyanate), and finally (C) aliphatic or cycloaliphatic diisocyanates which are modified by free radical grafting copolymerisation with vinyl monomers and which are obtained by polymerising in the presence of 100 parts of the diisocyanate from 10 up to 100 parts, preferably from 20 up to 75 parts, of a vinyl monomer, preferably methyl methacrylate, with the aid of a free radical polymerisation initiator, for example an organic peroxide, such as benzoyl peroxide, tert.-butyl peroctoate and the like, or an aliphatic azo compound, such as azoisobutyronitrile. In addition to the diisocyanates already mentioned, aliphatic diisocyanates having a linear carbon chain, for example hexamethylene diisocyanate, are also suitable for use as the graft substrate. It has been shown that aliphatic diisocyanates modified in this manner lead to polyurethane-urea elastomers, which are soluble in monomeric methyl methacrylate to give a clear solution and give clear polymers when the refractive indices of the polymer phase and viscous phase are correctly matched.

Isophorone diisocyanate and hexamethylene diisocyanate or isophorone diisocyanate which have been modified by graft copolymerisation with methyl methacrylate and have a polymer content of up to 50%, preferably of up to 40%, are preferably used.

Suitable relatively long-chain diols with 2 terminal hydroxyl groups in the molecule are preferably polyesters, polyethers, polyacetals, polycarbonates, polyesteramides and polyamides of molecular weight 400–6,000, which preferably have a glass transition temperature $\leq -20°$ C. Polyester diols and polyether-diols are particularly preferred.

Examples of possible polyesters containing hydroxyl groups are reaction products of dihydric alcohols with dibasic carboxylic acids. Instead of the free polycarboxylic acids, it is also possible to use the corresponding polycarboxylic acid anhydrides or corresponding polycarboxylic acid esters of lower alcohols or mixtures thereof for the preparation of the polyesters. The polycarboxylic acids can be of an aliphatic, cycloaliphatic, aromatic and/or heterocyclic nature and can be optionally substituted, for example by halogen atoms, and/or unsaturated. Examples of the polycarboxylic acids and derivatives thereof which may be mentioned are; succinic acid, adipic acid, suberic acid, azelaic acid, sebacic acid, phthalic acid, isophthalic acid, phthalic anhydride, tetrahydrophthalic, anhydride, hexahydrophthalic anhydride, tetrachlorophthalic anhydride, endomethylenetetrahydrophthalic anhydride, glutaric anhydride, maleic acid, maleic anhydride, fumaric acid, dimeric fatty acids, such as oleic acid, terephthalic acid dimethyl ester and terephthalic acid bis-glycol ester. Examples of possible polyhydric alcohols are ethylene glycol, propylene 1,2-glycol and 1,3-glycol, butylene 1,4-glycol- and 2,3-glycol, hexane-1,6-diol, octane-1,8-diol, neopentylglycol, cyclohexanedimethanol (1,4-bis-hydroxymethylcyclohexane), 2-methyl-1,3-propanediol and furthermore diethylene glycol, triethylene glycol, tetraethylene glycol, polyethylene glycols, dipropylene glycol, polypropylene glycols, dibutylene glycol and polybutylene glycols. Polyesters from lactones, for example ε-caprolactone, or hydroxycarboxylic acids, for example ω-hydroxycarproic acid, can also be employed.

The possible polyethers containing two hydroxyl groups are also those of the type which is in itself known, and are prepared, for example, by self-polymerisation of epoxides, such as ethylene oxide, propylene oxide, butylene oxide, tetrahydrofurane, styrene oxide or epichlorohydrin, for example in the presence of $BF_3$, or by addition of these epoxides, optionally as a mixture or successively, to starting components reactive hydrogen atoms, such as alcohols or amines, for example water, ethylene glycol, propylene 1,3-glycol or 1,2-glycol, 4,4'-dihydroxy-diphenylpropane or aniline. Those polyethers which predominantly contain (up to 90% by weight, relative to all the OH groups present in the polyether) primary OH groups are particularly preferred.

Examples of possible polyacetals are the compounds which can be prepared from glycols, such as diethylene glycol, triethylene glycol, 4,4'-dihydroxyethoxy-diphenyldimethylmethane and hexanediol, and formaldehyde. Polyacetals which are suitable according to the invention can also be prepared by polymerisation of cylic acetals.

Possible polycarbonates containing hydroxyl groups are those of the type which is in itself known, which can be prepared, for example, by reacting diols, such as propane-1,3-diol, butane-1,4-diol and/or hexane-1,6-diol, diethylene glycol, triethylene glycol or tetraethylene glycol, with diaryl carbonates, for example diphenyl carbonate, or phosgene.

Suitable diamines for the chain lenghening are alkylenediamines with 2 to 36 C atoms, for example hexamethylenediamine, undecamethylenediamine, or 2,2,4- or 2,4,4-trimethyl-1,6-diaminohexane or industrial mixtures thereof, diamines derived from dimeric fatty acids with up to 36 C atoms and furthermore cycloaliphatic diamines with 5 to 25 C atoms, for example the various diaminocyclohexanes, diaminohexahydro-toluenes and diaminodicyclohexylmethanes, either in the form of the pure position isomers and geometric isomers or as industrial isomer mixtures, and also 1-amino-3,3,5-trimethyl-5-aminomethylcyclohexane (isophoronediamine). The latter diamine is preferably used.

Compounds which are monofunctional towards isocyanate, for example alcohols or amines, are used as chain stoppers for any free isocyanate groups which may still be present after the chain lengthening. These compounds can be saturated, which is frequently preferred, or olefinically unsaturated. In the latter case, the unsaturated groups thus introduced into the polyurethane-urea can participate in the polymerisation of the methyl methacrylate, by means of which bonding between the polymer phase and the viscous phase is achieved. Examples of suitable and preferred saturated chain stoppers are lower aliphatic alcohols, preferably with 1-4 C. atoms, such as methanol, ethanol or butanol, or aliphatic monoamines, preferably with 1,6 C atoms, such as butylamine, dibutylamine or cyclohexylamine. Compounds which are suitable for introducing double bounds capable of undergoing polymerisation are, for example, allyl alcohol (preferred), allylamine or, preferably, hydroxyalkyl esters (with 2-4 C. atoms in the alkyl group) of α,β-unsaturated carboxylic acids with 3-5 C atoms, such as 2-hydroxyethyl methacrylate (preferred).

For their processing by the powder-/liquid process in dentistry, the polyurethane-elasticated methacrylates are mixed with the monomer to form a paste. Methyl methacrylate is preferably used as the monomer. Monomers which contain two or more double bonds in the molecule and which thus lead to crosslinking are added in order to increase the resistance to solvents and the abrasion resistance. The following compounds, for example, can be added as crosslinking agents in amounts of 0.1% by weight to 30% by weight, preferably 1% by weight to 15% by weight: ethylene glycol dimethacrylate, triethylene glycol dimethacrylate, butanediol dimethacrylate, trimethylolpropane trimethacrylate, bis-GMA, methylene-bis-acrylamide, triacrylformal and the bifunctional comonomers mentioned in U.S. Pat. No. 3,730,947.

The resulting compositions consisting of bead polymer and monomer can be hardened using initiator systems, based on peroxides or aliphatic azo compounds, which release free radicals. Examples of suitable polymerisation initiators are diacyl peroxides, such as, for example, dibenzoyl peroxide, or alkylacyl peroxides, such as, for example, tertiary butyl perpivalate, optionally in the presence of accelerators, such as aromatic tertiary amines, for example alkylated anilines, toluidines or xylidines. Cobalt salts or copper salts as well as compounds from the bartiburate group and sulphinic acids and sulphones can also be used as accelerators.

Whilst hardening at elevated temperature can be carried out by means of peroxides alone, such as dibenzoyl peroxide, chlorobenzoyl peroxide, toluyl peroxide or lauryl peroxide, or by means of free radical initiators alone, such as, for example, azoisobutyric acid nitrile or azoisobutyric acid esters, it is necessary to add accelerators in the case of hardening at low temperatures. 0.01% by weight to 2% by weight of polymerisation initiator are required in the case of hardening at elevated temperature. 0.02% by weight to 5% by weight of polymerisation initiators and 0.02% by weight to 5% by weight of accelerators are required in the case of hardening at low temperatures.

EXAMPLE 1

Dental beads are prepared, in the presence of a polyurethane, by a process for the bead polymerisation of methyl methacrylate.

A polyvinylpyrrolidone with a K value of 90 was used as the dispersing agent in the bead polymerisation and a mixture of lauroyl peroxide and dicyclohexyl percarbonate in the ratio 1:1 was used as the peroxidic initiator in an amount of 0.73%, relative to methyl methacrylate used (% by weight). The methyl methacrylate contained 9.9% of dissolved polyurethane.

The polyurethane is a diamine-lengthened polyester-polyurethane based on a mixture of two polyester-diols A and B.

Polyester-diol A consists of a polyester based on adipic acid, hexane-1,6-diol and neopentyl lycol, with a hydroxyl number of 66.

Polyester B is a polyester based on ethylene glycol, adipic acid and phthalic anhydride, with a hydroxyl number of 64.

Polyester A (0.35 equivalent) and polyester B (0.15 equivalent) are reacted with isophorone diisocyanate (0.75 equivalent); lengthening with isophoronediamine to the extent of 90% and termination with 2-hydroxyethyl methacrylate follow.

0.25% by weight of dibenzoyl peroxide are added to 15 parts by weight of the dental beads prepared in this manner and the mixture is made into a paste with 5.36 parts by weight of a liquid consisting of 94% by weight of methyl methacrylate and 6% by weight of ethylene glycol dimethacrylate. Sheets 2 mm thick are pressed from this paste and polymerisation is then carried out.

The polymerisation is carried out as follows: the water bath is heated to 70° C. in the course of 30 minutes, the temperature is kept constant for 30 minutes, the bath is then heated to 100° C. and this temperature is kept constant for a further 30 minutes. The cell is cooled in a water bath.

After removing from the cell, test pieces are cut out of the sheet without heating the sheet. The test pieces thus obtained are subjected to the Dynstat test according to DIN 53,452.

Test results: (in each case the mean value from 5 test pieces)
Impact strength: 50.77 kp/cm$^2$
Bending angle: 19°
Flexural strength: 1155 kp/cm$^2$
Ball indentation hardness 100": 1327 kp/cm$^2$
Ball indentation hardness 60": 1225 kp/cm$^2$

Comparison

As a control experiment, customary methyl methacrylate beads containing 0.25% by weight of dibenzoyl peroxide are polymerised with a liquid consisting of 94% of methyl methacrylate and 6% by weight of ethylene glycol dimethacrylate and the polymer is subjected to the strength test according to DIN 53,452:

Impact strength: 19.4 kp/cm$^2$
Bending angle: 18°
Flexural strength: 1059 kp/cm$^2$
Ball indentation hardness 10": 1249 kp/cm$^2$
Ball indentation hardness 60": 1158 kp/cm$^2$

What is claimed is:

1. A denture, crown, bridge or teeth prepared from an elasticized polymethacrylate obtained by bead polymerization of (A) 88 to 99.5% by weight of a polymer consisting of polymerized units of (1) at least one methacrylic acid ester with 1 to 10 C atoms in the aliphatic, saturated alcohol component, (2) of said methacrylic ester polymer containing up to 30% by weight of copolymerized units of at least one monomer from the group consisting of acrylic acid esters with 1 to 10 C atoms in the aliphatic, saturated alcohol component, hydroxyalkyl esters of acrylic acid or methacrylic acid with 2 to 4 C atoms in the alkyl group, styrene, vinyl acetate (meth)acrylamide, (meth)acrylic acid itaconic acid, and (B) 0.5 to 12% by weight of a diamine-lengthened polyurethane which has been obtained from
   (1) one or more substantially linear bifunctional hydroxyl compounds having a molecular weight of from 400 to 6000 and a glass transition temperature of $\leq -20°$ C. and selected from polyesters, polyethers, polyacetals, polycarbonates, polyesteramides and polyamides,
   (2) a diisocyanate from the group consisting of (a) an aliphatic diisocyanate with a branched carbon skeleton of 7 to 36 C atoms, (b) a cycloaliphatic diisocyanate and (c) an aliphatic or cycloaliphatic diisocyanate modified with a vinyl monomer by free radical grafting copolymerization, and
   (3) an aliphatic or cycloaliphatic diamine and a monofunctional chain terminator.

2. A process for preparing a denture, crown, bridge or teeth which comprises bead polymerizing (A) 88 to 99.5% by weight of a polymer consisting of polymerized units of (1) at least one methacrylic acid ester with 1 to 10 C atoms in the aliphatic, saturated alcohol component, (2) or said methacrylic ester polymer containing up to 30% by weight of copolymerized units of at least one monomer from the group consisting of acrylic acid esters with 1 to 10 C atoms in the aliphatic, saturated alcohol component, hydroxyalkyl ester of acrylic acid or methacrylic acid with 2 to 4 C atoms in the alkyl group, styrene, vinyl acetate (meth)acrylamide, (meth)acrylic acid and itaconic acid, and (B) 0.5 to 12% by weight of a diamine-lengthened polyurethane which has been obtained from
   (1) one or more substantially linear bifunctional hydroxyl compounds having a molecular weight of from 400 to 6,000 and a glass transition temperature of $\leq -20°$ C. and selected from polyesters, polyethers, polyacetals, polycarbonates, polyesteramides and polyamides,
   (2) a diisocyanate from the group consisting of (a) an aliphatic diisocyanate with a branched carbon skeleton of 7 to 36 C atoms, (b) a cycloaliphatic diisocyanate and (c) an aliphatic or cycloaliphatic diisocyanate modified with a vinyl monomer by free radical grafting copolymerization, and
   (3) an aliphatic or cycloaliphatic diamine and a monofunctional chain terminator.

3. A method according to claim 2 which comprises subjecting the bead polymer to moulding and hardening by the powder-liquid process.

4. A method for making a denture, crown, bridge or teeth which comprises subjecting to moulding and hardening by the powder-liquid process acrylate chips comprising elasticized polymethacrylate elasticized by means of diamine-lengthened polyurethane according to claim 2.

* * * * *